United States Patent [19]

Hinzmann

[11] 4,302,174
[45] Nov. 24, 1981

[54] ARRANGEMENT FOR CLOSING THE BARRELS OF TAMPON INSERTERS

[75] Inventor: Alfred Hinzmann, Richmond, Va.

[73] Assignee: Hauni-Richmond, Inc., Richmond, Va.

[21] Appl. No.: 93,119

[22] Filed: Nov. 13, 1979

[51] Int. Cl.³ .............................................. B29D 31/00
[52] U.S. Cl. .................................... 425/341; 264/296; 425/345; 425/392
[58] Field of Search ............... 425/340, 341, 345, 392, 425/454; 264/296

[56] References Cited

U.S. PATENT DOCUMENTS

| 647,993 | 4/1900 | Schmidt | 264/296 X |
| 999,183 | 7/1911 | Philpot | 425/392 |
| 3,190,944 | 6/1965 | Moore | 264/234 X |
| 3,694,859 | 10/1972 | Glasman | 425/340 |
| 4,104,013 | 8/1978 | Kelly | 425/340 X |

FOREIGN PATENT DOCUMENTS 752221 7/1956 United Kingdom ............... 425/392

Primary Examiner—Thomas P. Pavelko
Attorney, Agent, or Firm—Peter K. Kontler

[57] ABSTRACT

The serrated end portions of the barrels of catamenial tampon inserters are permanently deformed into a substantially hemispherical shape by applying heat and pressure thereto in depressions provided at the periphery of a container which accommodates a confined body of liquid, such as silicon oil, and a heating device which maintains the temperature of the body of liquid within a predetermined range. The heating device includes an electric heater which extends only over a part of the trajectory of movement of the deforming depressions. The barrel preforms are supplied to alternate depressions of an odd number of depressions and the final assemblies are discharged only after they have completed more than a full circle about the axis of rotation of the container.

10 Claims, 5 Drawing Figures

ARRANGEMENT FOR CLOSING THE BARRELS OF TAMPON INSERTERS

BACKGROUND OF THE INVENTION

The present invention relates to an arrangement for closing the end portions of catamenial tampon inserters.

In recent years, catamenial tampons have been gaining an increasing degree of popularity, especially among active women, as superior and more convenient substitutes for customary sanitary napkins. One reason for this is that they are imperceptible through garments, no matter how tight these garments may be. Another reason may be that, if properly used, they afford protection against the soiling of the garment or underwear, which is superior to that afforded by the sanitary napkins.

The tampons may be acquired as such, and they may be introduced manually without resorting to any auxiliary devices. However, this method of introduction is yielding, in an ever-increasing manner, to the use of tampon inserters, which are usually constructed as cylinder-and-piston, or telescoping, assemblies, and which are introduced with the respective tampon accommodated therein, whereupon the tampon is expelled therefrom and the empty tampon inserter is withdrawn.

While it is possible to so construct a tampon inserter as to be reusable over and over again, the current trend is toward the use of disposable tampon inserters which serve as protectors for the tampons during their handling at the manufacturing plant, such as packaging, and during the transportation and handling prior to actual use. After the tampon is expelled from the respective tampon inserter, the latter is discarded.

For the tampon inserter to be able to act as a protector, and to facilitate the introduction of the tampon inserter, it is already known, for instance, from the U.S. Pat. No. 3,895,634, to impart to the leading end portion thereof a hemispherical configuration. This reduces if not eliminates the danger of injury and existence of an unpleasant feeling during the introduction.

There are already known various machines for making the tampons, attaching withdrawal strings thereto, assembling the components of the tampon inserters, introducing the tampons into the tampon inserters, and closing the leading ends of the tampon inserters after the introduction of the tampons thereinto. However, experience has shown that the existing machinery operates at a rather slow pace and in a very cumbersome manner, which increases the manufacturing cost of the final articles both in terms of capital investment and labor costs, which necessarily reflects itself in the price of the final article.

OBJECTS AND SUMMARY OF THE INVENTION

It is an object of the present invention to so construct a machine for making tampon inserter-tampon assemblies as to render it possible to produce such assemblies at a speed which is higher than by resorting to the existing machinery.

Another object of the present invention is to provide an arrangement for closing the leading ends of the barrels of tampon inserters which is superior to those of the prior art.

A further object of the invention is to develop an arrangement for closing the leading ends of the barrels of tampon inserters which renders it possible to close such barrels in a reliable manner and in a highly reproducible and dependable way.

An additional object of the present invention is to so design the arrangement of this type as to be able to carry out the barrel-closing operation within a rather narrow temperature range.

A concomitant object of the invention is to so construct the barrel-closing arrangement as to be simple in construction, inexpensive to manufacture, reliable in operation, and capable of operating at a high speed.

One feature of the present invention resides in the provision of an arrangement for deforming objects, especially for closing the barrels of catamenial tampon inserters, which, comprises means for advancing a succession of objects through a treating station, including a carrier having a plurality of uniformly spaced treating locations, means for maintaining one of the objects at each of the treating locations and means for so moving the carrier that the treating locations advance at a predetermined speed and along a predetermined path through the treating station, means for supplying the objects in succession to the treating locations, and means for simultaneously heating and deforming a selected portion of each of the objects (such as the leading end portion of the barrel of the tampon inserter) during advancement of the respective treating location through the treating station, including a container accommodating a body of heat-transmitting liquid and having a portion facing the path of advancement of the treating location and provided with a succession of depressions which are uniformly spaced from one another, the same as the treating locations, and have a shape substantially corresponding to that desired for the selected portion (the leading end portion of the barrel), means for so displacing the container that the depressions pass through the treating station at the predetermined speed and in alignment with the treating locations, means for effecting relative displacement between an object and the aligned depression for introducing the selected portion of the object into the respective depression and withdrawing the same therefrom after deformation to the desired shape, and means received in the container and operative for heating the body of liquid.

Advantageously, the carrier and the container are substantially cylindrical and are mounted for rotation and, during the operation of the arrangement, actually rotate about a common preferably vertical axis. When the arrangement is constructed in this manner, it is particularly simple and easy to manufacture and service.

It is further advantageous when the heating means includes at least one electrical resistance heater which is at least partially immersed in the body of liquid in the vessel. By using an electrical resistance heater as the heating means, it is especially simple to supply the energy which is needed for heating the body of liquid in the container. While the construction of the carrier and the container as substantially cylindrical components is very advantageous, it is also possible and contemplated by the present invention to give them other configurations. Thus, the only requirement in this respect is that the paths of advancement of the treating locations and of movement of the depressions be parallel to one another, at least within the treating station. Even here, however, it is especially advantageous when the paths are closed and coextensive both within and without the treating station.

According to a presently preferred embodiment of the invention, the supplying means is so arranged as to supply objects to every other of an odd number of treating locations. Then, it is further advantageous to provide means for removing the objects from the respective treating locations after the objects have bypassed the supplying means which then supplies further objects to the intervening treating locations. When the carrier and the container are substantially cylindrical, the removing means is so constructed as to remove the objects from the respective treating stations only after such objects have covered more than a full circle about the common axis of the carrier and of the container. Advantageously, the removing means may be situated substantially diametrically opposite the supplying means.

The body of liquid may fill only a portion of the interior of the container. As a result of this, the upper level of the body of liquid may assume a configuration given by the interaction of gravitational and centrifugal forces, so that a smaller amount of the liquid may be used with the same heating effect (due to the movement of the liquid toward the periphery of the container where the depressions are located and the attendant increase of the amount of heat stored in the liquid at this region) as if the liquid filled the interior of the container in its entirety. Futhermore, air which is present above the upper level of the body of liquid in the interior of the container will act as a cushion which will permit the liquid to expand due to its heating without subjecting the walls of the container to undue stresses. Preferably, the liquid is silicon oil or a similar substance which has a high heat-storing capacity, a high coefficient of heat transmission, and which can withstand relatively high temperatures without deterioration.

The novel features which are considered as characteristic of the invention are set forth in particular in the appended claims. The improved arrangement itself, however, both as to its construction and its mode of operation, together with additional features and advantages thereof, will be best understood upon persual of the following detailed description of certain specific embodiments with reference to the accompanying drawing.

DESCRIPTION OF THE PREFERRED EMBODIMENTS

Figure 1:
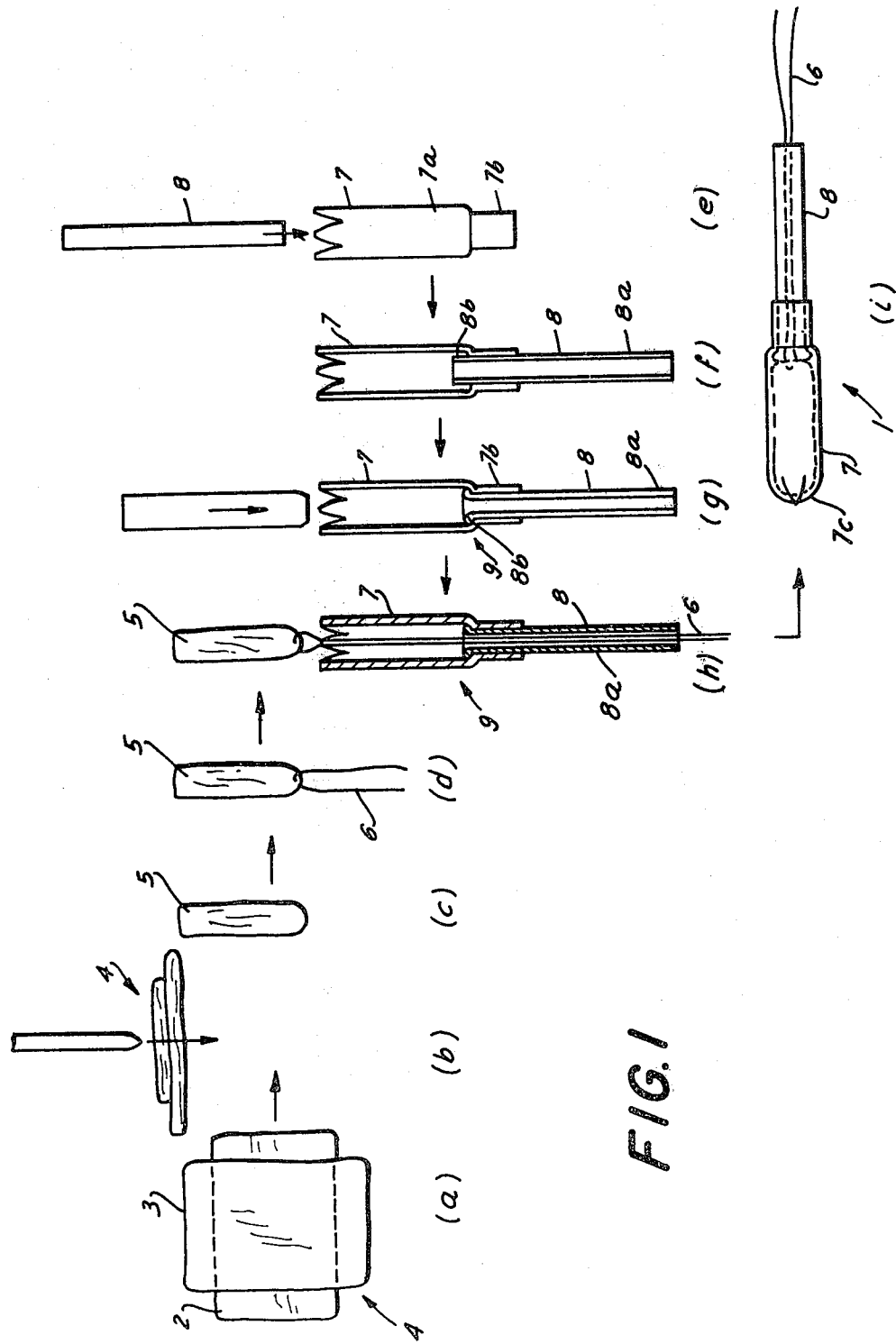
FIG. 1 is a diagrammatic representation of the steps which have to be performed in order to obtain a tampon inserter-catamenial tampon assembly.

FIG. 1 illustrates, in parts (a) to (i), a plurality of steps which are to be performed in a predetermined order to form a catamenial tampon-tampon inserter assembly 1 which is shown in its final form in part (i) of FIG. 1.

The assembly 1 is formed from a plurality of basic components, including two sections 2 and 3 of foraminous, preferably fibrous material, such as rayon. Such sections may be obtained by severing them from one or more continuous webs having the required dimensions. The sections 2 and 3 are superimposed upon one another in the manner illustrated in part (a) in top plan view to form a cross-shaped formation 4. Thereafter, the formation 4 is deformed, in the manner indicated in part (b) of FIG. 1 in side elevational view, to form a body or tampon 5 shown in part (c). Conversion of the formation 4 into the tampon 5 will involve the use of deforming tools. Preferably, the formation 4 is pushed into a confining sleeve in which it acquires a substantially cylindrical configuration.

In many instances, the tampon 5 must be cured after its formation, such as by heating to a predetermined temperature and for a predetermined period of time, for instance, to reduce the moisture content thereof. This operation, if needed, is performed between the operations shown in parts (c) and (d) of FIG. 2, advantageously while the tampon 5 is confined in the aforementioned or another confining sleeve.

After the formation of the tampon 5, or after the curing thereof, a withdrawal string 6 is attached thereto. This operation, the result of which is indicated in part (d) of FIG. 1, is preferably performed while the tampon 5 is held in the illustrated vertical position, so that the two sections of the string 6 will extend, due to forces, downwardly from the tampon 5.

The assembly 1 is further formed from a barrel 7 and a plunger 8 which, when assembled, together constitute a tampon inserter 9. The barrel 7 and the plunger 8 are supplied from different sources or storage arrangements to an assembling location, such as that shown in part (e) of FIG. 1. Prior to the delivery of the barrels 7 to the assembling location, they may have to be reoriented so as to assume positions corresponding to that illustrated in part (e).

Each barrel 7 has a larger-diameter main portion 7a, and a smaller-diameter end portion 7b. The plunger 8 is tubular and cylindrical when it reaches the assembling location. Thereat, it is introduced into the interior of the barrel 7 through the main portion 7a thereof, and into, and possibly to a certain extent but not entirely beyond, the end portion 7b. This is illustrated in part (f) of FIG. 1, where the reference numeral 8a denotes that portion of the plunger 8 which extends outwardly and beyond the end portion 7b of the barrel 7.

After the assembly of the plunger 8 with the barrel 7, that end 8b of the plunger 7 which is still received in the main portion 7a of the barrel 7 is flared, as indicated in part (g) of FIG. 1. The plunger 8 could be delivered to the assembling location in its flared condition; however, it has been found that the flaring of the end of the plunger 8 only after its assembly with the barrel 7 is advantageous in that the plunger 8 can be delivered to the assembing location in either of two orientations. This renders it unnecessary to resort to measures aimed at assuring that the plunger 8 is invariably supplied to the assembling station in one of these orientations. The flaring of the end 8b of the plunger 8 entails that the flared end 8b engages a shoulder which forms the transition between the main portion 7a and the end portion 7b of the barrel 7 and thus prevents the plunger 8 from continuing its movement in the direction of introduction into the barrel 7 through and beyond the end portion 7b. The flared end portion 8b does not prevent the plunger 8 from being expelled from the barrel 7 in a direction opposite to its introduction; however, this is not disadvantageous during the assembling operation since neither the barrel 7 nor the plunger 8 are subjected to any forces which would cause them to move relative to one another in opposite directions and so as to expel the plunger 8 from the barrel 7 through the main portion 7a of the barrel 7. On the other hand, the movement of the plunger 8 relative to the barrel 7 in this direction is needed for expulsion of the tampon 5 from the barrel 7 of the tampon inserter 9 when the latter is used.

The assembled inserter 9 and the tampon 5 provided with the withdrawing string 6 are brought together at an inserting station substantially in the position shown in part (h) of FIG. 1. This means that, if the tampon 5 is formed, or the tampon inserter 9 is assembled, in any other orientation than that shown, it will have to be reoriented or turned before it reaches the inserting station. At this station, both the tampon 5 and the inserter 9 are substantially vertical, the inserter 9 being located below the tampon 5 with its barrel 7 situated at a level above the plunger 8. The string 6 extends downwardly from the lower end portion of the tampon 5 to which it is attached and, as shown in part (h) of FIG. 1, it is introduced into and passes through the tampon inserter 9, preferably beyond the portion 8a of the plunger 8. The string 6 can be introduced into the tampon inserter 9 by applying subatmospheric pressure to the lower end of the plunger 8 so that the string 6 is pulled into the tampon inserter 9 by suction.

When the string 6 is fully accommodated in the inserter 9, the tampon 5 is introduced into the interior of the main portion 7a of the barrel 7, such as by being pushed from above into the barrel 7. Advantageously, if the string 6 is pulled into the tampon inserter 9 by suction, subatmospheric pressure at the lower end of the plunger 8 is maintained while the tampon 5 is being introduced into the barrel 7. This not only causes the string 6 to continue its movement in a substantially taut condition and without tangling toward, into and beyond the plunger 8, but also aids in the introduction of the tampon 5 into the barrel 7 by establishing between the two ends of the tampon 5 a pressure differential which acts in the direction of introduction of the tampon 5 into the barrel 7.

Once the tampon 5 is fully accommodated in the interior of the main portion 7a of the barrel 7, an end portion 7c which is situated longitudinally opposite to the smaller-diameter end portion 7b of the barrel 7 is closed. To this end, such end portion 7c is provided with prefabricated serrations which are so shaped that, once they are bent to assume a substantially hemispherical shape as shown in part (i) of FIG. 1, they will substantially complement one another without leaving any, or by leaving only small, slots therebetween. At least the barrel 7 is made of a thermoplastic or thermosetting synthetic plastic material, and a permanent deformation of the serrations into their final positions is achieved by simultaneously subjecting them to heat and deforming pressure. Of course, the serrations forming the end 7c of the barrel 7 must remain flexible enough to permit their yielding during use of the tampon inserter 9 out of the way of the tampon 5 which is being ejected from the barrel 7 by displacing the plunger 8 relative to the barrel 7 in a direction opposite to the direction of introduction into the barrel 7.

Figure 2:
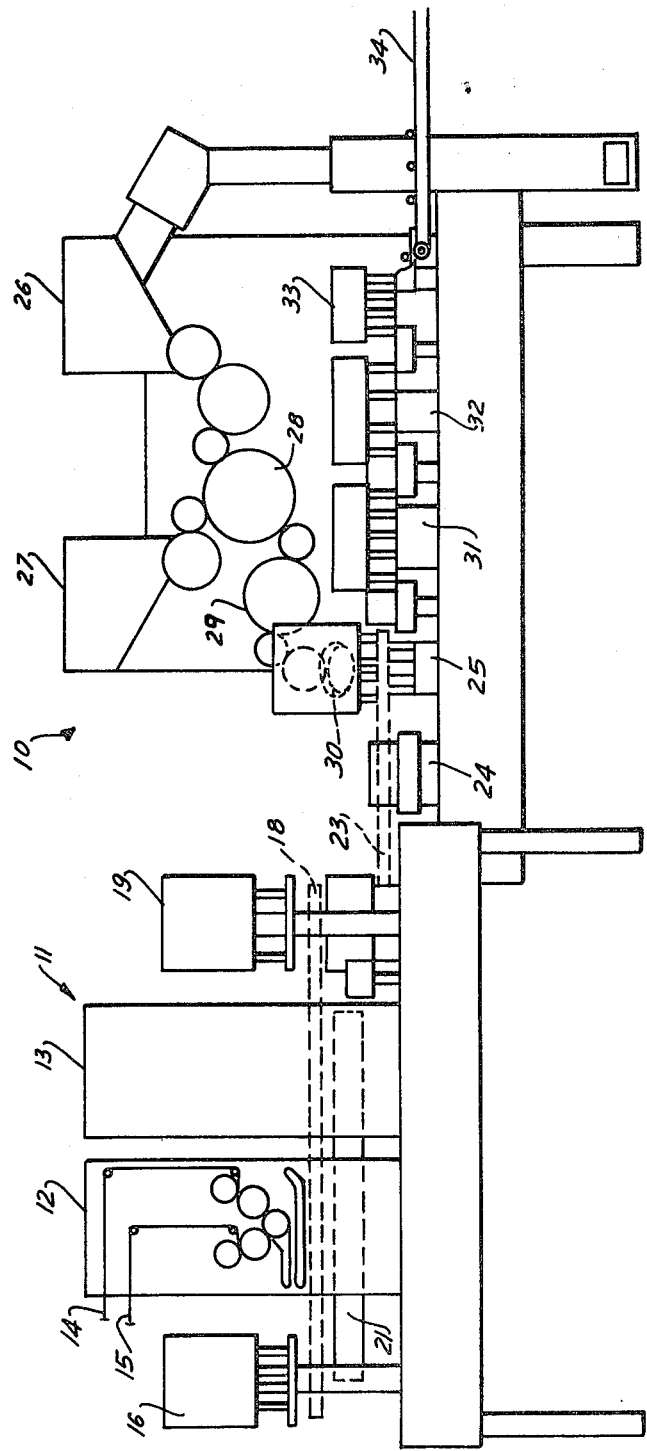
FIG. 2 is a side elevational view of an apparatus capable of performing the steps which have been indicated in FIG. 1 and including the arrangement of the present invention.
Figure 3:
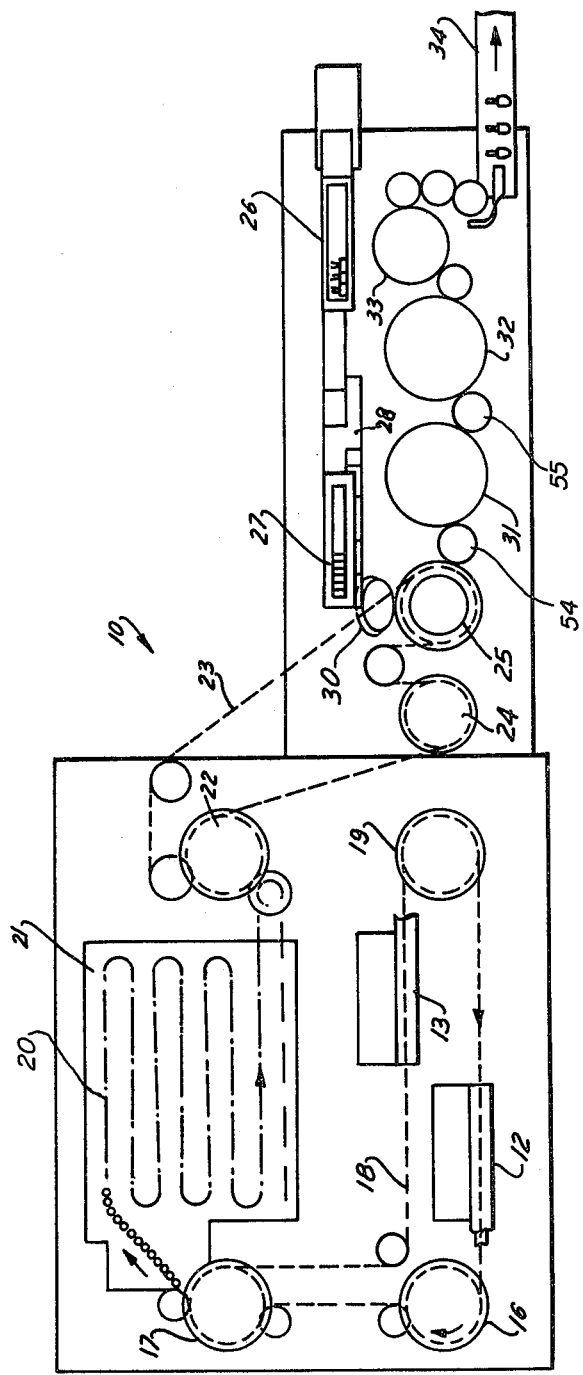
FIG. 3 is a top plan view of the apparatus of FIG. 2.

A machine 10 which is capable of performing all of the above-mentioned operations and more and in which the present invention is embodied is shown schematically in FIGS. 2 and 3. This machine 10 includes a cutting arrangement 11 consisting of two cutting towers 12 and 13. The cutting tower 12 is supplied with two webs 14 and 15. The same holds true for the cutting tower 13; however, since the tower 13 is identical or at least similar to the cutting tower 12, no details of the tower 13 have been shown in the drawing.

Each of the cutting towers 12 and 13 cuts individual sections 2, 3 from the webs 14 and 15 (and the corresponding webs supplied to the cutting tower 13) and superimposes the same upon one another to form assemblies 4 of the type indicated in FIG. 1. From the cutting tower 12, the respective assemblies 4 are supplied to a deforming station 16 where the assemblies 4 are converted, in succession, into the tampons 5. From there, the tampons 5 travel to a transfer station 17. An endless conveyor 18, preferably a chain, transports the tampons 5 between the stations 16 and 17. The cutting tower 13 operates in the same manner, but the assemblies 4 formed therein are supplied to another deforming station 19 where the assemblies 4 are converted into a further succession of tampons 5 and transferred to the same conveyor 18. The operation of the cutting tower 12 is synchronized with the operation of the tower 13 in such a way that the tampons 5 formed at the deforming station 16 will alternate with those formed at the deforming station 19.

At the transfer station 17, the tampons 5 are transferred to another conveyor 20 which transports the tampons 5 through a curing oven 21. The conveyor 20 advances the tampons 5 through the curing oven 21 along a meandering path delivers the tampons 5 to another transfer station 22 where the cured tampons 5 are transferred to a further conveyor 23 which transports the tampons 5 to a string-attaching station 24 where a string 6 is attached to each tampon 5. From here, the conveyor 23 advances the tampons 5 to an assembling station 25 where the tampons 5 are assembled with the tampon inserters 9.

Referring now particularly to FIG. 2, the apparatus 10 further includes two storage hoppers 26 and 27. The hopper 26 accommodates a supply or properly oriented barrels 7, and the hopper 27 accommodates a supply of plungers 8 each of which assumes one of two permissible orientations. The barrels 7, on the one hand, and the plungers 8, on the other hand, are discharged by the respective storage hoppers onto a series of transporting rollers which eventually bring the barrels 7 and the plungers 8 together in substantial axial alignment with one another on an inserting drum 28. The barrels 7 and the plungers 8 are assembled with one another at respective inserting locations of the inserting drum 28. The assemblies of the barrels 7 and plungers 8 are then transferred, in succession, to a flaring drum 29 where the end portions 8b of the plungers 8 are flared in the manner and for the purpose discussed above.

It will be noted that the conveyor 23 delivers the tampons 5 to the assembling station 25 in their proper vertical orientation, that is, with the string 6 hanging downwardly from the lower end portion of the tampon 5. On the other hand, upstream of the assembling station 25, the barrels 7 and the plungers 8 and eventually their assemblies or tampon inserters 9 are conveyed in substantially horizontal positions as far as their longitudinal axes are concerned. Hence, the tampon inserters 9 have to be reoriented prior to feeding them into the assembling station 25. To this end, there is provided a transfer disk 30 which rotates about an axis substantially halving the angle between the planes along which the tampons 5, on the one hand, and the tampon inserters 9, on the other hand, move. The tampon inserters 9 are transferred, downstream of the flaring drum 29, to the transfer disk 30 and their orientation is changed to correspond to that of the tampons 5 during orbiting of inserters 9 on the transfer disk 30 about the aforementioned inclined axis.

During travel through the assembling station 25, the tampons 5 are introduced into the barrels 7 of the consecutive tampon inserters 9 in the manner which has been discussed before. Then, the tampon inserters 9, with the tampons 5 properly accommodated therein, are transferred to a heating drum 31 wherein heat and pressure are applied to the serrated end portions 7c of the barrels 7 to deform and close the same. Advantageously, the closed tampon inserters 9 are then transferred to a cooling drum 32 wherein the previously heated end portions 7c of the barrels 7 of the tampon inserters 9 are cooled to remove the heat accumulated in such end portions 7c and to cause them to lose their heat-induced plasticity. The closing of the end portion 7c of the barrel 7 converts the partially finished assembly of the tampon 5 with the tampon inserter 9 into the final tampon-tampon inserter assembly 1.

It is further advantageous when, after leaving the cooling drum 32, the assemblies 1 are transported through another station 33 where they may be tested, for instance, for proper closing of the end portion 7c, for the presence of the string 6 and its extension outwardly of the plunger 8, or for other parameters or features, or where, for instance, a minute quantity of perfume may be injected into the assembly 1 and onto the tampon 5 accommodated therein, if such operations have not already been performed upstream of this station 33. After leaving the station 33, the assemblies 1 are reoriented so as to extend substantially horizontally and, in this position, they are discharged onto a conveyor 34, such as a conveyor belt, which carries them out of the machine or apparatus 10, for instance, to a packaging location or the like.

Having so described the steps performed in, and the basic construction of, the apparatus 10, the construction of the arrangement of the present invention and its cooperation with the other constituent parts of the apparatus 10 will now be discussed with reference to FIGS. 4a and 4b.

Figure 4A:
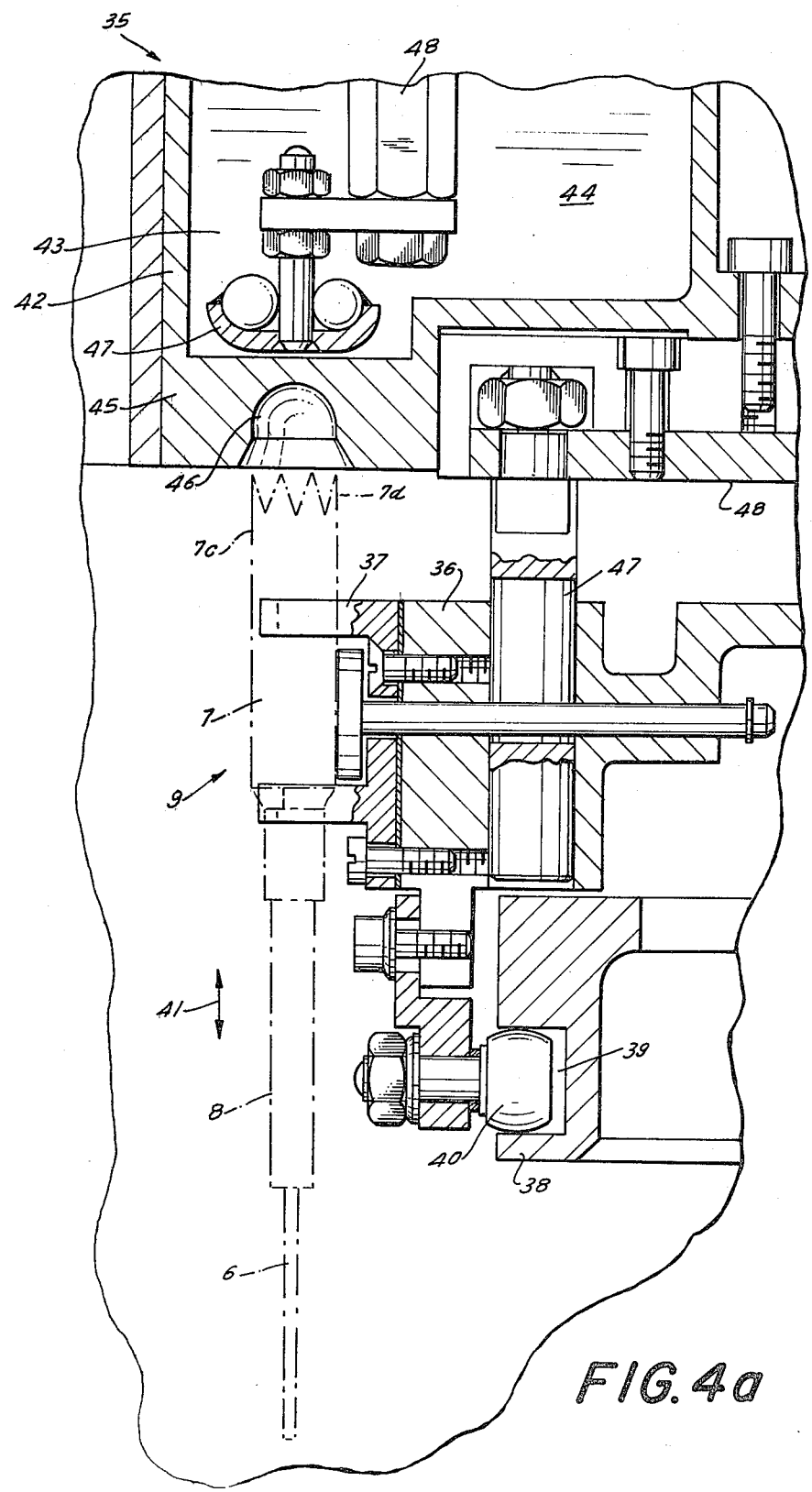
FIG. 4a is a fragmentary axial sectional view of the arrangement according to the present invention taken at the beginning of a region in which the barrels are being closed.
Figure 4B:
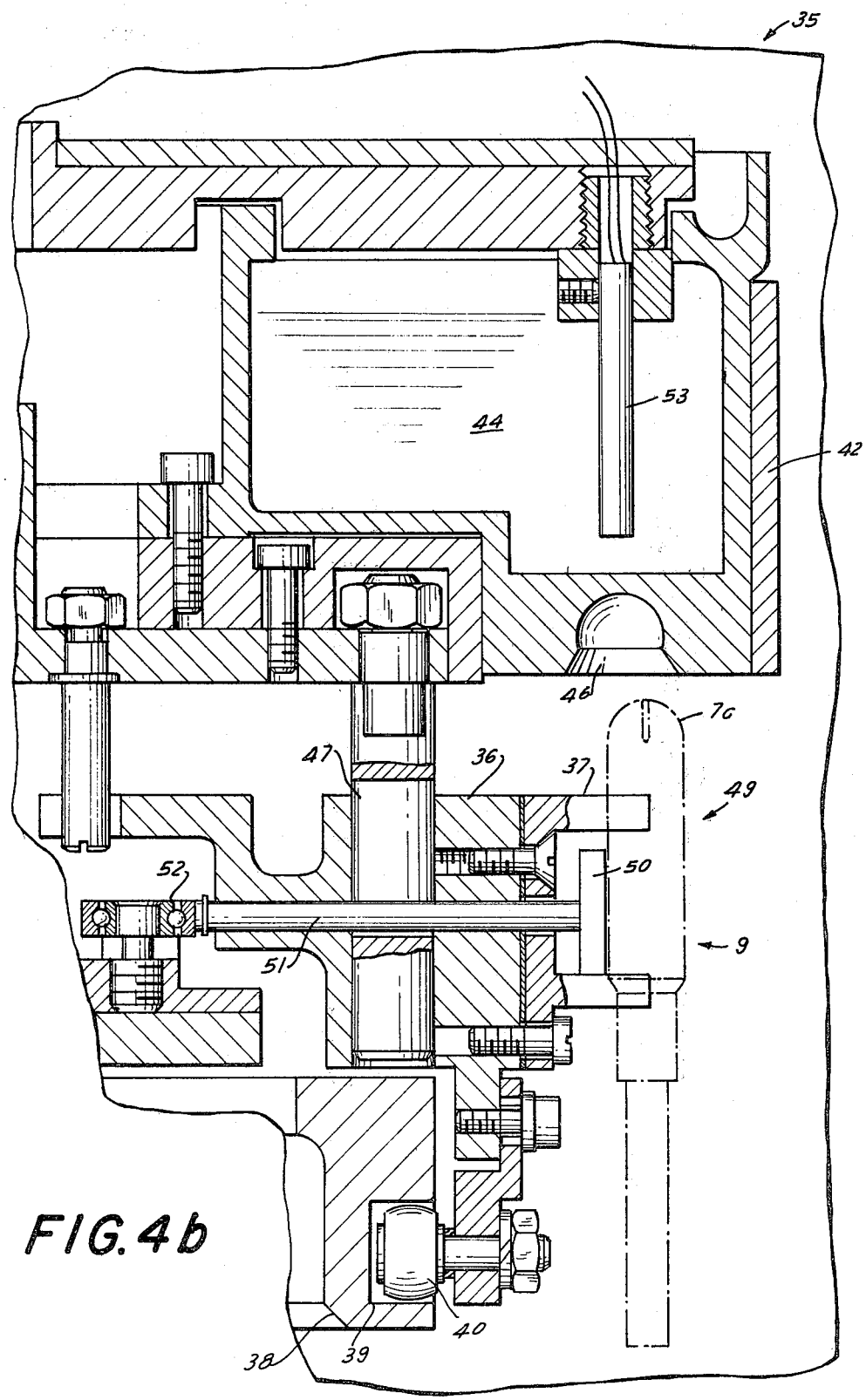
FIG. 4b is a view similar to that of FIG. 4a but taken at the downstream end of such region.

In FIGS. 4a and 4b, the reference numeral 35 denotes the arrangement of the present invention in its entirety. In each of these views, only that fragment of the arrangement 35 is illustrated, and only those components have been identified by reference numerals, which are needed for understanding of the present invention.

As illustrated in FIG. 4a, the arrangement 35 includes a mounting drum 36 which has a plurality of depressions 37 at its periphery, each constituting a treating location for a tampon inserter 9 which is indicated by phantom lines. As mentioned before, the barrel 7 of the respective tampon inserter 9 has a plurality of serrations, indicated at 7d, at its upwardly extending end portion 7c. When the tampon inserter 9 reaches the arrangement 35, a tampon 5 is already accommodated therein and the withdrawal string 6 extends downwardly beyond the plunger 8 of the tampon inserter 9. The tampon inserters 9 may be held in the respective depressions 37 in any conventional manner (which has not been illustrated, such as a guide rail partially surrounding the mounting drum 36 at the level of the depressions 37. However, it is also conceivable that each barrel could be held in the respective depression by suction or in a similar manner.

The mounting drum 36 is rotatably mounted and is rotated by driving means of a conventional construction which has not been illustrated, such as an electric motor and/or a transmission. A stationary cam member 38 is situated below the mounting drum 36 and has a peripheral groove 39 which acts as a cam track. A preferably rotatable cam follower 40 is mounted, on the mounting drum 36 and is received in the groove 39 so as to follow the cam track defined by the cam member 38. The groove 39 is elongated and circumferentially complete, or at least substantially so, and so configurated as considered in its longitudinal direction (that is, in the circumferential direction of the cam member 38) that it guides the cam follower 40 for movement not only in the circumferential direction of the cam member 38, but also in the axial directions of the mounting drum 36, that is, in the directions indicated by the doubleheaded arrow 41. Inasmuch as the cam follower 40 is mounted on the mounting drum 36, and the latter is movable in the axial direction thereof, the mounting drum 36 will perform axial movements determined by the movement of the cam follower 40 in one or the other of the directions indicated by the arrow 41. The tampon inserter 9 which is received in the respective depression 37 of the mounting drum 36 will share the up and down movement of the mounting drum 36. At the location illustrated in FIG. 4a, the mounting drum 36 assumes its lower position.

A container 42 is situated above the mounting drum 36 and extends to above the trajectory of movement of the tampon inserters as they orbit with the mounting drum 36 about the axis of the latter. The container 42 defines a chamber 43 in which there is accommodated a stagnant body 44 of heat-transmitting liquid, such as silicone oil or a similar liquid which is capable of storing and transmitting heat.

The container 42 has a bottom wall 45 which includes at least one deforming depression 46 that is aligned with the respective inserter 9 at least while the end portion 7c thereof is received therein. While it would be possible to so construct the arrangement that it would only have one or a small number of deforming depressions 46, it is currently preferred that the container 42 rotate with the mounting drum 36 about the axis of the latter, such that the deforming depressions 46 are in constant alignment with the depressions 37 of the mounting drum 36 and, consequently, with the respective tampon inserters 9 received in the respective depressions 37.

A temperature influencing heating device 47 is accommodated in the chamber 43 and is immersed in the body of liquid 44. At least theoretically, the heating device 47 could share the rotary movement of the container 42 about the common axis; however, it is currently preferred that the heating device 47 be stationary. In an advantageous, currently preferred embodiment of the present invention, the heating device 47 is constructed as an elongated rail which is mounted on a mounting arrangement 48. The heating device 47 need not, and preferably is not, circumferentially complete; rather, it extends only over such regions of the bottom wall 45 where heat is to be supplied to the latter. Of course, any heat generated by this heating device will also reach other regions of the container 42, especially of the bottom wall 45 thereof, due to conduction in the material of the container 42, and due to conduction and convection in the body of liquid 44. Nevertheless, the heating device 47 is preferably arranged at those regions where the heating effect is to be most intense, that is, at and possibly upstream of the regions where the end portions 7c of the barrels 7 enter the deforming depressions 46 of the bottom wall 45 of the container 42.

Advantageously, the heating device 47 is constructed as an electric resistance heater to which electric energy is supplied in a conventional manner, such as through the mounting arrangement 48. The electric current flowing through the heating device 47 will elevate the temperature of the latter and also heat the body of liquid 44 in addition to heating the bottom wall 45 of the container 42.

As the mounting drum 36 is raised upwardly, as a result of the cooperation of the cam follower 40 with the cam track 39, the upper end portion 7c of the barrel 7 which has the serrations 7d formed thereon will enter the respective depression 46 and the serrations 7d will be deformed as they slide along the surface bounding the respective deforming depression 46, into a substantially hemispherical shape. The heat applied to the serrations through the surface of the bottom wall 45 which bounds the respective deforming depressions 45 will plasticize the material of the serrations 7d so that the latter will undergo a permanent deformation. Then, as the mounting drum 36 is lowered, and with it the tampon inserter 9, the end portion 7c of the barrel 7 will leave the deforming depression 46, but it will keep its substantially hemispherical shape, that is, the serrations 7d will not return to their original positons.

The mounting drum 36 could be made of one piece and include all the depressions 37. However, it is currently preferred that the mounting drum be constituted by a number of individual sections, one for each of the depressions 37. Each of these sections is then individually guided on a guiding rod 47 or a similar guiding element which, in the illustrated embodiment, is rigidly connected to a wall 48 which, in turn, is rigidly connected to the bottom wall 45 of the container 42. Thus, the connecting rods 47 orbit about the axis of the container 42 during the rotation of the latter, and so do the sections of the mounting drum 36.

FIG. 4b illustrates similar parts as FIG. 4a, but is taken at a different region so that is also shows some other parts which have not been shown in or discussed in connection with FIG. 4a. FIG. 4b illustrates the situation existing after the end portion 7c of the barrel of the tampon inserter 9 has already been closed. At such time, the end portion 7c has already left the deforming depression 46, as the cam follower 40 received in the cam track 39 has caused the respective section of the mounting drum 36 to descend on the guiding rod 47 to its lowermost position.

So, for instance, FIG. 4b shows an ejector 49 by means of which the finished tampon inserter 9 is expelled from the respective depression 37. The ejector 49 includes an enlarged head 50 which engages the inserter 9, and an actuating rod 51 which is displaceably mounted in the section of the mounting drum 36 and which cooperates with a stationary cam 52, shown in FIG. 4b as having the form of a ball-bearing, which engages the rod 51 when the section of the mounting drum 36 reaches an ejecting location and displaces the rod 51 in such a direction (radially outwardly) so as to dislodge the inserter 9 and expel the same from the respective depression 37. The provision of the ejector 49 renders it is possible, if desired, to omit any external means for holding the inserters 9 in the respective depressions 37 of the mounting drum 36, inasmuch as they could be simply forced into the corresponding depressions 37 and the friction between the same and the surfaces bounding the respective depressions 37 would be sufficient to hold the inserters 9 in the depressions 37 until the ejector 49 becomes active and ejects the inserter 9 from the associated depression 37.

FIG. 4b also shows that a temperature measuring sensor 53, such as a sheated thermocouple, extends into the body of liquid 44 and measures the temperature thereof in a conventional manner. The signal derived from this sensor 53 is preferably used to directly control the operation of the heating device 47.

The arrangement 35 which has been discussed above forms part of the arrangement 31 shown, for instance, in FIG. 3 which is flanked by and cooperates with a supply transfer device 54 and a discharge transfer device 55. The supply transfer device 54 is so constructed that it supplies tampon inserters 9 only to every other of the depressions 37. On the other hand, the ejector 49 may be so constructed, in accordance with the present invention as to eject the inserters 9 only from the same depressions upstream of the supply transfer device 54. This can be achieved, for instance, by moving the cam 52 between an extended position in which it engages the rod 51, and a retracted position in which it bypasses the next following rod 51. Under these circumstances, the number of the depressions 37 and of the deforming depressions 46 is odd. In each instance, the respective tampon inserter 9 will be expelled from its depression 37 only after it has traversed more than a full circle about the axis of the mounting drum 36. In this situation, if the cam member 38 were stationary, the end portion 7c would enter and leave the respective deforming depression 46 twice. If it is desired to let the end portion 7c enter the depression 46 only once and stay therein for more than a full circle, it is contemplated, for instance, to rotate the cam member 38 in the same direction as, but at a fraction of the speed of, the mounting drum 36 and of the container 42. Preferably, the fraction amounts to one-half so that the cam follower 40 performs a full circle relative to the the cam member 38 when the mounting drum 36 and the container 42 have performed two full rotations. This can be achieved by using a transmission which is interposed between a prime mover, such as an electromotor, the container 42 and/or the cam member 38.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

I claim:

1. An arrangement for closing the barrels of catamenial tampon inserters, comprising means for advancing a succession of barrels in a predetermined direction, at a predetermined speed and along a predetermined path, including a carrier having a plurality of equidistant treating locations and means for releasably holding the barrels at said locations; means for supplying barrels to said locations in a first portion of said path; and means for simultaneously changing the temperature of and deforming a selected portion of each of the barrels during advancement of the respective location along a second portion of said path, including a container for a body of heat-exchanging liquid, said container having a portion adjacent to said path and a succession of uniformly spaced depressions each having a shape substantially complementary to the desired shape of selected portions of the barrels, means for moving said container in synchronism with said carrier so that successive depressions register with successive locations in a second portion of said path, means for effecting relative displacement between successive barrels and the corresponding depressions so as to introduce the selected portions of such barrels into and to thereupon withdraw deformed selected portions from the corresponding depressions during travel of barrels at said locations toward, past and beyond said second portion of said path, and stationary temperature influencing means extending into said container and operative to influence the temperature of the liquid in said container.

2. The arrangement as defined in claim 1, wherein said liquid is silicon oil.

3. The arrangement as defined in claim 1, wherein said carrier and said container are substantially cylindrical and are mounted for rotation about a common axis.

4. The arrangement as defined in claim 1, wherein said temperature influencing means includes at least one electrical resistance heater which is at least partially immersed in the body of liquid in said container.

5. The arrangement as defined in claim 1, wherein said path is closed and said depressions move along a second closed path which is parallel to said first mentioned closed path.

6. The arrangement as defined in claim 5, wherein said supplying means is operative to deliver barrels to alternate locations of said carrier and the latter has an odd number of locations, and further comprising means for removing the barrels from the respective locations downstream of said second portion of said path.

7. The arrangement as defined in claim 6, wherein said carrier and said container are substantially cylindrical and are mounted for rotation about a common axis, said removing means being operative to remove the barrels after the barrels have completed more than a full circle about said common axis.

8. The arrangement as defined in claim 7, wherein said removing means is situated substantially diametrically opposite said supplying means.

9. The arrangement as defined in claim 7, wherein said common axis is vertical.

10. The arrangement as defined in claim 1, wherein said body of liquid only partially fills said container and said temperature influencing means includes first and second portions which are respectively immersed into and located outside of such body of liquid.

* * * * *